(12) United States Patent
De Gaulle et al.

(10) Patent No.: US 7,776,601 B2
(45) Date of Patent: Aug. 17, 2010

(54) METHOD FOR DETERMINING AND MONITORING AGEING OF BLOOD BAGS

(75) Inventors: Antoine De Gaulle, Sevres (FR); Jean-Claude Mongrenier, Saint Germain en Laye (FR)

(73) Assignee: Biolog, Boulogne Billancourt (FR)

( * ) Notice: Subject to any disclaimer, the term of this patent is extended or adjusted under 35 U.S.C. 154(b) by 424 days.

(21) Appl. No.: 10/480,390

(22) PCT Filed: Jun. 10, 2002

(86) PCT No.: PCT/FR02/01968

§ 371 (c)(1), (2), (4) Date: Apr. 14, 2004

(87) PCT Pub. No.: WO02/100462

PCT Pub. Date: Dec. 19, 2002

(65) Prior Publication Data

US 2004/0166583 A1    Aug. 26, 2004

(30) Foreign Application Priority Data

Jun. 12, 2001  (FR)  .................................. 01 07618

(51) Int. Cl.
*G01N 31/00*   (2006.01)
*G01N 15/06*   (2006.01)
*G01N 35/02*   (2006.01)
*G01N 9/30*    (2006.01)

(52) U.S. Cl. .................. 436/1; 436/8; 436/16; 436/20; 436/50; 436/55; 422/68.1; 422/72; 422/74; 422/75; 422/102; 422/105

(58) Field of Classification Search .................. 604/408
See application file for complete search history.

(56) References Cited

U.S. PATENT DOCUMENTS 4,415,802 A * 11/1983 Long ........................... 235/382
4,441,329 A *  4/1984 Dawley ....................... 62/126

(Continued)

FOREIGN PATENT DOCUMENTS

| FR | 2777378 | 10/1999 |
| FR | 2796182 | 1/2001 |
| WO | 00/45331 | 8/2000 |
| WO | 03/033052 | 4/2003 |

OTHER PUBLICATIONS

English Language Abstract of FR 2 825 637.

*Primary Examiner*—Jill Warden
*Assistant Examiner*—Neil Turk
(74) *Attorney, Agent, or Firm*—Greenblum & Bernstein, P.L.C.

(57) ABSTRACT

The invention concerns a method which consists in determining ageing an ageing index of a blood bag (11, 62), to determine whether the blood bag is or not suitable for transfusion to a patient. The ageing index is calculated by connecting a silicon chip provided with a loop antenna integral with the blood bag (11, 62) with an electronic communication device (2, 8, 17, 12, 20, 24), itself equipped with a loop antenna, connected to a computer (9, 13) containing appropriate computing software elements. Said ageing index is regularly calculated at the blood transfusion center (16) from the sample (1), until it is removed from storage (7) to be sent to the health-care institution (18) and to the operating theatre (19).

3 Claims, 3 Drawing Sheets

U.S. PATENT DOCUMENTS

| | | |
|---|---|---|
| 4,859,360 A | 8/1989 | Suzuki et al. |
| 5,193,855 A * | 3/1993 | Shamos ...................... 283/117 |
| 5,507,525 A * | 4/1996 | Leuenberger ................ 283/67 |
| 5,572,873 A * | 11/1996 | Lavigne et al. ............... 62/3.62 |
| 5,628,204 A | 5/1997 | Shanaberger |
| 5,798,694 A * | 8/1998 | Reber et al. ................. 340/540 |
| 5,969,606 A | 10/1999 | Reber et al. |
| 6,113,554 A | 9/2000 | Gilcher et al. |
| 6,285,285 B1 | 9/2001 | Mongrenier |
| 6,402,702 B1 | 6/2002 | Gilcher et al. |
| 6,712,276 B1 * | 3/2004 | Abali et al. .................. 235/492 |
| 6,929,061 B2 * | 8/2005 | Lajeunesse .................. 165/202 |
| 2002/0013523 A1 * | 1/2002 | Csore et al. .................. 600/368 |
| 2002/0143320 A1 | 10/2002 | Levin |
| 2003/0072676 A1 | 4/2003 | Fletcher-Haynes et al. |
| 2004/0044326 A1 * | 3/2004 | Kranz et al. ................. 604/408 |
| 2004/0230337 A1 | 11/2004 | De Gaulle et al. |
| 2005/0068182 A1 | 3/2005 | Dunlap et al. |

* cited by examiner

METHOD FOR DETERMINING AND MONITORING AGEING OF BLOOD BAGS

CROSS-REFERENCE TO RELATED APPLICATIONS

The present application is a National Stage Application of International Application No. PCT/FR02/01968, filed Jun. 10, 2002. Further, the present application claims priority under 35 U.S.C. §119 of French Patent Application No. 01/07618 filed on Jun. 12, 2001.

BACKGROUND OF THE INVENTION

1. Field of the Invention

The invention concerns a method for determining and monitoring the ageing of blood bags in blood transfusion centers and health-care institutions.

2. Discussion of Background Information

At the present time, blood bags are collected in blood transfusion centers; each bag is dated at the time the blood is collected, which indicates the beginning of the life-span of the bag and the by-products, life-span that lasts a predetermined length of time; blood collected in bags is subjected to filtering, centrifugation and separation, which leads notably to production of a by-product which is a bag of red cells intended for transfusion whose life-span is forty five days beginning at the date on which the blood was collected; the bags of red blood corpuscles are stored in blood transfusion centers and delivered according to the requirements of health-care institutions. It sometimes occurs that bags of red blood corpuscles, which had been prepared as precautionary measures for an operation are not used; as it is impossible at present to have a firm guarantee of the quality of the contents of the bag of red blood corpuscles, with a view of them being re-used, the bag is destroyed. As destruction of unused bags of red blood corpuscles represents at present a loss of twelve percent of the blood bags collected, it is essential to reduce this wastefulness.

As the bags of red blood corpuscles are at present transported between the blood transfusion centre and the health-care institution without any special precautions, a study is under way with a transport company for guaranteeing the continuity of the cold chain between these two establishments; in this case, the blood bag is placed in a refrigerated container inside which a device is placed indicating the temperature in the container throughout transport; as the bags of red blood corpuscles are placed in an appropriate refrigerator on arrival at the health-care institution, these bags can be returned to the blood transfusion centre if they have not been removed from the refrigerator in the mean time, to be placed at the disposal of a surgeon.

When the blood is collected, it is transferred into a main blood bag connected to a filter, itself connected to a primary blood bag; the primary blood bag is part of a group of bags that also include three secondary bags to which it is connected by flexible tubing arranged in parallel; the blood from the main blood bag is filtered and introduced into the primary blood bag; the primary blood bag is centrifuged in order to separate the red cells, platelets and serum which are then respectively transferred into each of the three bags and the bag containing the red cells is the one used to carry out blood transfusions. As a reminder, platelets are isolated only when there is a specific supply requirement—otherwise they remain with the red cells and only two secondary bags are used.

A traceability device for blood bags, as per patent application FR-9804802 is under development; it integrates a silicon chip with the blood bag; each silicon chip is fitted with a loop antenna which communicates with the loop antenna on an electronic communication device, connected to a computer, capable of supplying the silicon chip on the one hand with energy and on the other with data which it stores in memory and which it is capable of restoring to the said computer through the electronic communication device; a mother silicon chip is attached to the mother blood bag which receives all the data concerning the donor and the results of analyses that have enabled the mother blood bag to be qualified; the electronic mother chip is fixed on a rectangular-shaped flexible chip support several centimeters long, on which a metallized loop circuit is printed that forms the communications loop antenna; in a preferred version of the invention, the flexible chip support for the primary silicon chip is placed on one of the largest surfaces of the mother blood bag beneath a rectangular label covering the major part of one of the principal surfaces; preferably the mother chip support is always put in the same place in relation to the label for facilitating positioning of the antenna on the electronic communication device. A patent application FR-9908887 describes a weighing and stirring device fitted with an electronic communication device which enables the blood donor's particulars and blood collection conditions to be recorded in the electronic mother chip on the mother blood bag; the blood in the mother blood bag is transferred through a filtration unit into the primary blood bag; the primary blood bag comprises a primary silicon chip to which the data contained in the electronic mother chip is transferred together with information on filtration conditions; the primary blood bag is then centrifuged; the constituents are separated and are introduced into the secondary blood bags; secondary blood bags are equipped with secondary silicon chips, identical to the mother and primary silicon chips, which are fixed to a flexible chip support placed under a label covering one side of the secondary blood bag, preferably in such a position that, when the mother, primary and secondary blood bags are placed above each other, the mother and primary silicon chip supports do not cover each other or the secondary flexible chip supports; information is entered into the secondary silicon chips on the secondary bags, in other words the red cell bag, the serum bag and possibly the platelet bag, by transferring data from the primary silicon chip on the primary blood bag, and completing it with data concerning the parameters used for separating the blood constituents. Concerning any red cell bag that has been used for a blood transfusion, at the end of the bag's use, the secondary silicon chip integrated into it contains information concerning its conditions of use and notably the identity of the patient who has received the transfusion.

SUMMARY OF THE INVENTION

The method, according to the invention, provides for formalizing, throughout its existence, the status of a mother, primary or secondary blood bag, referred to hereafter as "blood bag", equipped with a silicon chip, in relation to the phenomenon of biodegradation which is qualified hereafter as "ageing", so that, at any given time and in the most accurate manner possible, it may be known whether the blood bag is qualified for use in a transfusion.

The invention also provides for a method of qualifying, re-qualifying and disqualifying a blood bag that includes a permanently attached a silicon chip fitted with a loop antenna capable of communicating with an electronic communication device, wherein the method comprises establishing an ageing index of the blood bag when blood is collected from a donor in a blood transfusion center, entering on the silicon chip, using the electronic communication device, a value of the ageing index as the ageing index evolves progressively towards a maximum value, which, when reached, leads to the blood bag being disqualified, calculating the value of the ageing index between two successive moments in time of a period of time by taking into account the following: bacteriological analyses; the value of the ageing index at the beginning of the period; a duration of the period; and environmental characteristics of the blood bag during the period under consideration. The ageing index is calculated when the blood bag enters or leaves a controlled atmosphere chamber and when a patient is transfused with the blood contained in the blood bag. A new ageing index value is entered in the silicon chip after each calculation.

The ageing index can be calculated using pre-determined ageing models characteristic of the period under consideration and established by experiment on a basis of empirical formulae. The ageing index can be calculated when the patient is transfused in a health-care institution. The establishing may comprise establishing the ageing index of the blood bag at an initial moment when blood is collected from a donor in a blood transfusion center. The method may further comprise determining and monitoring an evolution of an ageing index of the blood bag so that a determination can be made as to whether or not the blood bag can be used to transfuse a patient. The electronic communication device may be equipped with a loop antenna connected to one of a computer and a calculating device. The electronic communication device is coupled to a weighing and stirring device. The ageing index may evolve progressively towards the maximum value depending on the time elapsed and environmental conditions. The ageing index may be calculated when the blood bag enters or leaves a controlled atmosphere chamber at the blood transfusion center and further comprising, when needed, recalculating the ageing index when stocks of blood bags are controlled for statistical reasons and when the blood bag is removed to be dispatched to a health-care institution. The electronic communication device may be connected to a computer and wherein the recalculating utilizes another electronic communication device connected to the computer. The calculating may comprise calculating automatically at close and regular intervals of time, whereby the blood bag may be removed at any moment after an up-to-date ageing index has been entered on the silicon chip and dispatched to an operating theater. The electronic communication device may be connected to a computer and wherein the establishing occurs before a patient is transfused with the blood contained in the blood bag using another electronic communication device connected to another second computer. The method may further comprise one of: placing an unused blood bag back into the controlled atmosphere chamber; and returning an unused blood bag to the blood transfusion center. The method may further comprise checking, at the moment of transfusion, a qualification of the blood bag using another independent electronic communication device. The other independent electronic communication device may be connected to a calculating system that is capable of comparing a length of time spent by the blood bag outside the controlled atmosphere chamber with an allocated length of time which corresponds to a life-span remaining in a non-controlled atmosphere outside the controlled atmosphere chamber. The method may further comprise, when the blood bag is determined to no longer be usable for transfusions, re-qualifying the blood bag using the electronic communication device connected to a computer. The controlled atmosphere chamber may be a cellular controlled atmosphere chamber and further comprising using a computer to manage a stock of blood bags inside the cellular controlled atmosphere chamber, whereby each compartment of the cellular controlled atmosphere chamber is allocated an address. The computer may be structured and arranged such that a user requiring the blood bags can enter requirements on the computer and provide a user identity, and the computer indicates in reply addresses of the compartments corresponding to the entered requirements. The blood bag may be located in one of a number of compartments of the controlled atmosphere chamber and the method may further comprise determining when the value of the ageing index the blood bag arranged in the controlled atmosphere chamber has exceeded the maximum value and indicating with a computer an address of the compartment containing the blood bag so that the blood bag identified for destruction.

The invention also provides for an arrangement for implementing the method described above, wherein the arrangement comprises: a cellular controlled atmosphere chamber having compartments for storing blood bags, one of the compartments comprising a horizontal lower surface capable of holding a blood bag, a loop antenna integrated in the horizontal lower surface in such a way that the loop antenna of the silicon chip can be located opposite the loop antenna of the compartment, and a dedicated electronic communication device integrated into the horizontal lower surface. The dedicated electronic communication device is connected to a computer.

Each compartment may comprise a lower horizontal surface having an integrated loop antenna and a dedicated electronic communication device connected to the computer, whereby the computer stores characteristics of the blood bags contained in the compartments and checks every compartment at regular intervals in time to determine whether a blood bag is in fact present in each compartment and calculates an ageing index so that the ageing index can be incorporated in the silicon chip of each blood bag with a time and a date of the calculation. The compartments may be arranged within a storage unit capable of being put inside the controlled atmosphere chamber. The compartments may comprise independent drawers having a back, side faces with guide rails arranged on outside surfaces, and the independent drawers may run on horizontal slide-ways attached to rack arrangements. The independent drawers may be arranged within a storage unit capable of being put inside the controlled atmosphere chamber. The compartments may include indicator lamps, whereby the indicator lamps act to identify compartments containing a disqualified blood from compartments that do not contain a blood bag or from compartments whose dedicated electronic communication device is not operational.

The invention also provides for a method of qualifying, re-qualifying and disqualifying a blood bag that includes a silicon chip and a loop antenna capable of communicating with an electronic communication device, wherein the method comprises entering on the silicon chip, using the electronic communication device, a value of the ageing index as the ageing index evolves progressively from when blood is collected from a donor in a blood transfusion center towards a maximum value, which, when reached, leads to the blood bag being disqualified, calculating, at different points in a period of time, the value of the ageing index by taking into account the following: bacteriological analyses; the value of the ageing index at the beginning of the period; a duration of the period; and environmental characteristics of the blood bag during the period under consideration. The calculating occurs when the blood bag enters or leaves a controlled atmosphere chamber and when a patient is transfused with the blood contained in the blood bag.

A new ageing index value can be entered in the silicon chip after each calculation.

The invention also provides for a method of qualifying, re-qualifying and disqualifying a blood bag that includes a silicon chip and an antenna capable of communicating with an electronic communication device, wherein the method comprises entering on the silicon chip, using the electronic communication device, a value of the ageing index as the ageing index evolves progressively from when blood is collected from a donor towards a maximum value, which, when reached, leads to the blood bag being disqualified, calculating, at different points in a period of time, the value of the ageing index by taking into account the following: bacteriological analyses; the value of the ageing index at the beginning of the period; a duration of the period; and environmental characteristics of the blood bag during the period under consideration. The calculating occurs when the blood bag enters or leaves a controlled atmosphere chamber and when a patient is transfused with the blood contained in the blood bag.

DETAILED DESCRIPTION OF THE INVENTION

The method provides for determining an ageing index for the blood bag, which defines the blood bag's qualification or unsuitability for being used or not used for transfusion to a patient; the blood bag is then hereafter said to be "qualified" or "unsuitable". The ageing index is calculated by putting the silicon chip on the blood bag in relation with an electronic communication device itself connected to a computer containing appropriate computing software elements. This index evolves progressively, depending notably on the blood bag's age and environmental conditions, towards a maximum value which, when it is reached, leads to the blood bag being declared unsuitable and being destroyed. Variation in this ageing index is calculated between two successive moments in time constituting a period, using a model referred to hereafter as "predetermined ageing model" that characterizes the period under consideration and which is established by experiment, based on empirical formulae taking into account the results of bacterial analyses, the blood bag's environment during the period under consideration and parameters such as the time and/or the temperature and value of the ageing index at the beginning of the period. This ageing index is initiated when the blood is collected, the date of which is recorded in the silicon chip on the primary blood bag; this supposes that a weighing and stirring device 1 (FIG. 1) supporting the blood bag is fitted with a first electronic communication device 2 which enables the date and time of blood collection to be recorded on the silicon chip on the primary blood bag, as well as data and particulars concerning the donor and blood collection conditions. The ageing index is calculated each time the blood bag changes its environment, for example at entry 3 and 5 and exit 4 and 6 of a storage zone, where atmospheric parameters are monitored, referred to hereafter as "controlled atmosphere chamber" 7 at which occasion the new ageing index value is recorded on the silicon chip on the blood bag and the blood bag is referred to as "re-qualified" if the ageing index is lower than its maximum value: otherwise it is unsuitable. Such an operation can be carried out manually when the blood bag is extracted from a controlled atmosphere chamber 7 by using a second electronic communication device 8 connected to an initial computer 9 containing the appropriate software elements. Such an operation can also be carried out automatically in a controlled atmosphere chamber where the silicon chip of each blood bag ills placed in permanent relation with a dedicated electronic communication device 12 connected to a second computer 13 containing the appropriate software elements. This type of controlled atmosphere chamber is referred to hereafter as "cellular controlled atmosphere chamber" 10. In these conditions the blood bag 11 can be taken out at any time after its ageing index has been updated on its silicon chip.

Figure 1:
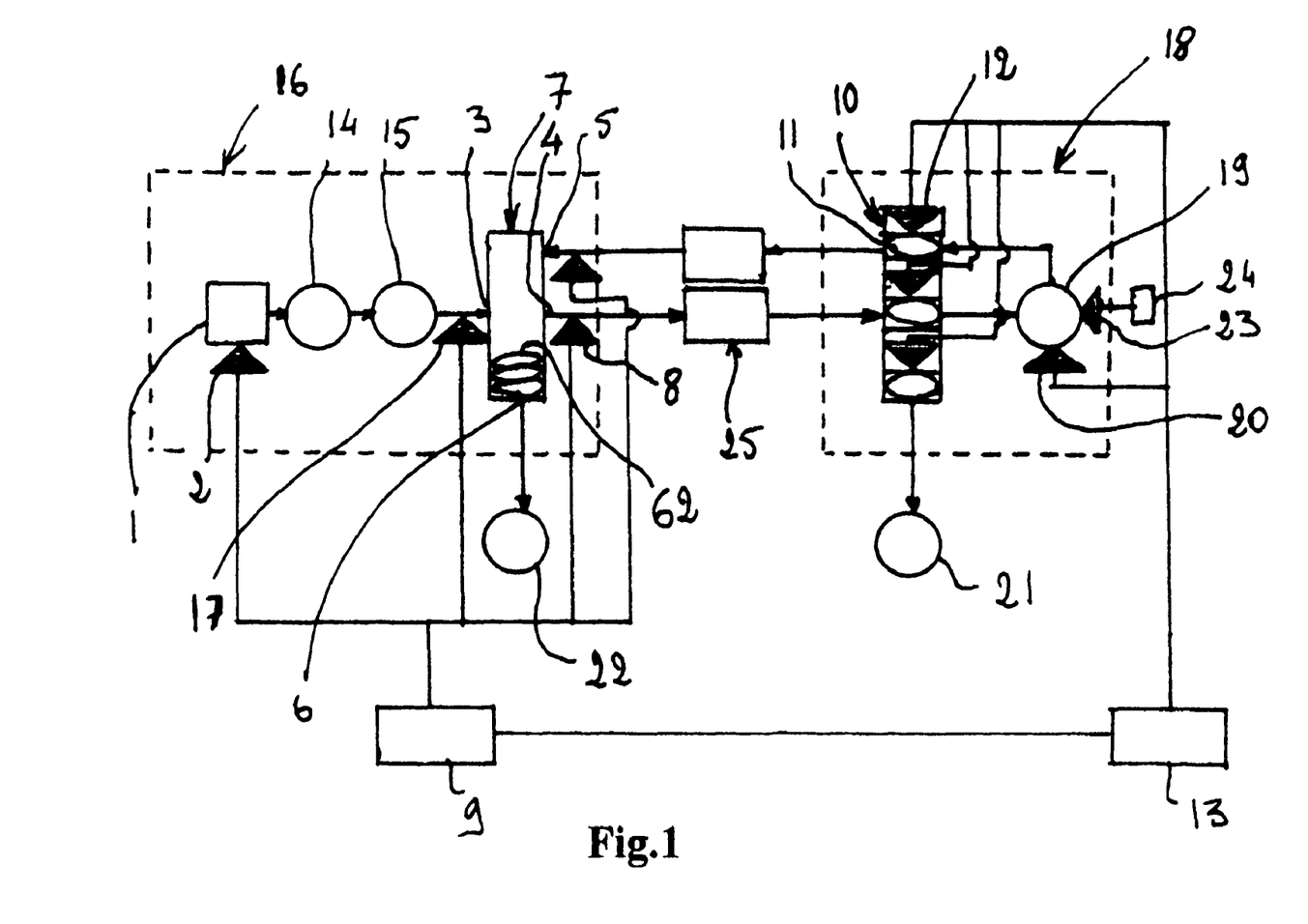
FIG. 1 represents a schematic diagram of the various phases through which a blood bag may pass using the method of the invention.

For example: when blood is collected, the initial time is recorded by the weighing and stirring device 1 on the primary silicon chip on the primary blood bag, which is then processed in a centrifugal separator 14. During the separation phase 15, the red cells are fed into one of the three secondary bags to constitute the blood bag; the data contained in the primary silicon chip is transferred to the silicon chip on the blood bag at the same time as data concerning centrifugation and separation. The blood bag is then directed to the controlled atmosphere chamber 7 of the blood transfusion center 16 and an initial ageing index value is calculated by placing its silicon chip in communication with an initial computer 9 via a third electronic communication device 17. During storage in the controlled atmosphere chamber 7, the blood bag 62 is not in principle monitored from an ageing point of view other than for statistical controls on the state of stocks, at which time the ageing index is updated for the blood bag that has been controlled 62. When the blood bag 62 is removed for a transport operation 25 to a health-care institution 18, the ageing index is updated, compared to the date of the last ageing index update using the second electronic communication device 8. Ageing indexes are then updated in the health-care institution 18 successively on entry in the cellular controlled atmosphere chamber 10 and later at close and regular intervals until blood bag 11 is removed to be directed to an operating theatre 19 where it is rechecked for the last time before transfusion by way of a fourth electronic communication device 20. If the blood bag is not used, it is returned to the cellular controlled atmosphere chamber 11 and even back to the blood transfusion centre 16 following the same procedure as the procedure described above.

When the blood bag 11 is in a cellular controlled atmosphere chamber 10 of a health-care institution 18, the silicon chip associated with each blood bag 11 is connected permanently to the second computer 13 belonging to the health-care institution 18 through a dedicated electronic communication device 12. At regular intervals, the second computer 13 checks the presence of the blood bag 11 in the cellular controlled atmosphere chamber 10 and the temperature therein in order to calculate the ageing of the blood bag 11 compared with tables of values established by experiment. The ageing calculation can be made, for example, by determining two parameters—the temperature and the time that has elapsed since the last update. An average temperature is determined which is weighted depending on its intrinsic value and depending on the time under consideration related to the initial time, determined on the weighing and stirring device 1 when the blood was collected. This weighted average temperature is then integrated in relation to the time to provide a value that measures the variation in the ageing index. To carry out the update operation, the new ageing index value is recorded on the silicon chip together with the date and time it was determined.

A maximum ageing index value is determined by experiment, which automatically leads to the unsuitability and destruction 21, 22 of the blood bag when the maximum value is reached.

When the blood bag 11 is removed from a cellular controlled atmosphere chamber 10, the silicon chip includes the value of the last ageing index calculated and the date and time at which this was done. If this blood bag 11 is made available in an operating theatre 19, the latter is equipped with the fourth electronic device 20 for communicating with the silicon chip on the blood bag which can read the value of the ageing index at the date of the last control. As, in principle, the temperature is no longer controlled from the moment the blood bag is taken from the cellular controlled atmosphere chamber 10, a mean evolution curve of the temperature is drawn up by experiment, depending on the time, which contributes to establishing pre-determined ageing model enabling the ageing index to be updated. If the fourth electronic communication device 20 is connected to the second computer 13 it is the latter which calculates the new ageing index which is validated and recorded on the silicon chip. If a fifth independent electronic communication device 23 serving to control the blood bag at the time of the blood transfusion is not connected to a computer, as may be the case when blood from the blood bag is transfused during transport of a person after an accident, it can be equipped with simplified way of calculation 24 giving information as to whether the bag is still qualified without however recalculating the ageing index; in fact a safety margin can be defined for the ageing index, when the index gets close to its maximum value, defined by the blood bag's remaining life-span in non-controlled atmosphere. If the blood bag 11 has used part of its remaining life-span during a period when it was in the controlled atmosphere chamber 10, it is disqualified and sent away for destruction 21. If the fifth independent electronic communication device 23 detects that the time allowed after the blood bag has left the cellular controlled atmosphere chamber 10 has elapsed, the blood bag is declared doubtful and must be re-qualified by putting it into communication with a dedicated electronic communication device 12 or the fourth electronic communication device 20 connected to the second computer 13. If the blood bag has not been used and is returned to the cellular controlled atmosphere chamber 10, the continuous ageing measurement method is re-initiated after calculating how much the blood pocket 11 has aged during its exposure to non-controlled atmosphere, using a pre-determined ageing model such as the one described above and the blood bag is either re-qualified or disqualified and sent away for destruction 21. Several pre-determined aging models can be defined for keeping as close as possible to the realities of the ageing process depending on the conditions under which the blood bag has been manipulated: manipulations concern the blood collection phase, the constituent centrifugation 14 and separation 15 phases, the transport-under-controlled-atmosphere phase 25 between the transfusion centre 16 and the health care institution 18.

Figure 2:
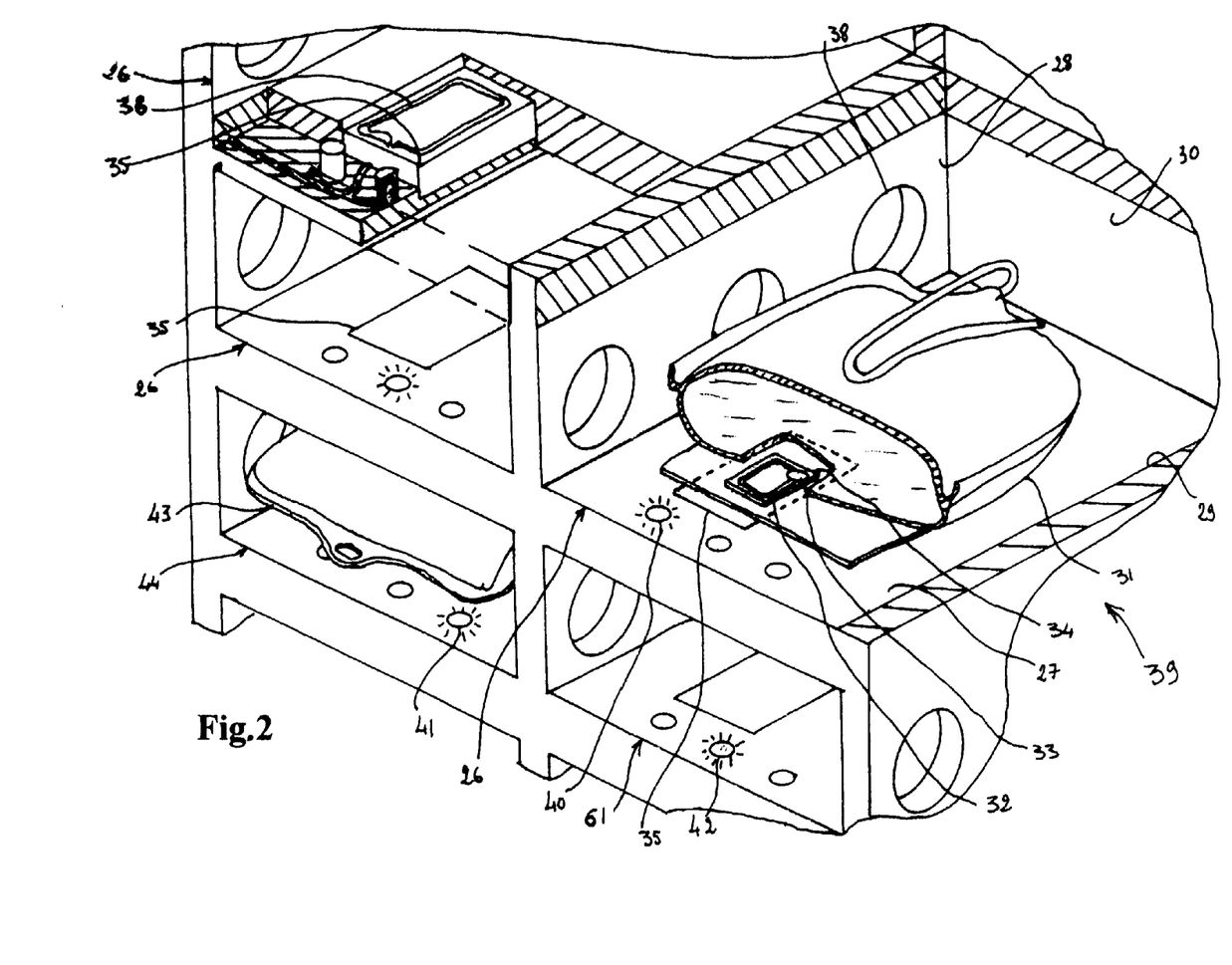
FIG. 2 represents a partial blown-up view of a storage device for blood bags fitted with an automatic device for monitoring blood bag ageing.

In a preferred version of the device for implementing the method, in the health-care institution 18, blood bag storage 11 is done in a cellular controlled atmosphere chamber 39 made up of a number of virtually parallelepiped compartments 26 (FIG. 2). The compartments 26 notably include a very wide and horizontal lower surface 27 surrounded by three small side surfaces 28, 29, 30 for holding a blood bag 31 and keeping it in position so that the loop antenna 32 of the silicon chip 33, fixed to a flexible silicon chip support 34 is opposite the loop antenna 36 of a dedicated electronic communication device 35 integrated into the wide horizontal surface 27. This supposes that the flexible silicon chip support 34 is always in the same position under a label 37, as described above and that the latter is always turned towards the wide horizontal lower surface 27. The compartments 26 are cut-out with openings 38 to allow cooling air to circulate from one compartment to another; each dedicated electronic communication device 35 is connected to the same computer that memorizes all or part of the characteristics of the blood bags 31 contained in compartments 26 and examines each compartment 26 at close and regular intervals in time to check that the blood bag 31 is in fact present in the compartment 26 and to calculate its ageing index so that this index can be integrated into the silicon chip 33 with the date and time when the calculation was made.

Blood bag stock management in the cellular controlled atmosphere chamber 39 is preferably carried out by the computer using an address allocated to each compartment 26 and a certain number of hierarchical criteria. The person responsible for taking out the blood bags enters the characteristics of his or her requirement onto the computer screen and, notably, gives his or her identity and the computer indicates in reply the addresses of the compartments 26 containing the blood bags 31 that correspond to the requirement and to the hierarchical criteria for removing them. The fact that the blood bags are really removed is controlled by detecting that the compartment 26 is empty; removing blood bags from compartments 26 other than those indicated for removal immediately sets off an alarm. The end of the removal operation gives rise to the issue of an electronic receipt on behalf of the person responsible for removing the bags.

Blood bags 43 contained in the cellular controlled atmosphere chamber 39, which have reached the maximum ageing index are downgraded and indicated on the computer screen so that they can be removed from their compartment for destruction.

Concerning blood bags being put into a cellular controlled atmosphere chamber 39, they are placed in empty compartments 26. The computer detects that a compartment that was previously empty is now occupied as it can read the silicon chip 33 placed under the label 37 of the blood bag 31. It can manage its ageing process on the basis of information contained in the silicon chip 33, for example, in the case of health-care institutions it will detect the course of its existence by reading the silicon chip 33. if the blood bag arrives from the transfusion centre 16 (FIG. 1) it updates the ageing index and puts the blood bag in the waiting list for an operation. If the blood bag comes back from the operating theatre 19, it must be re-qualified and repositioned depending on hierarchical criteria, either for return to the blood transfusion centre 16, for disqualification and destruction 21, or for return to the waiting list for a new operation.

To facilitate filling compartments 26 (FIG. 2) and removing blood bags 31, compartments may be equipped with colored indicator lamps, for example, a green indicator lamp 40 that lights up when a compartment 26 contains a blood bag 31 that has been selected for removal. A red indicator lamp that lights up when the computer detects that a compartment 44 contains a blood bag that is no longer valid 43. Possibly a white indicator lamp for an empty compartment 61 can be utilized. The latter white indicator lamp 42 will reveal a dysfunction in the dedicated electronic communication device 35 or the silicon chip 33, if ever it lights up on a compartment that contains a blood bag. By lighting up when a blood bag 31 or 43 is inserted, the green 40 or red 42 indicator lamp indicates that the computer has taken the blood bag's characteristics into account.

On a practical level, the compartments 26 in a cellular controlled atmosphere chamber 39 may be elements that are part of a larger unit, which is placed inside a non-equipped cellular controlled atmosphere chamber. Compartments 26 are preferably made from plastic reinforced with a minimum amount of metal elements and are sufficiently far apart vertically for the loop antenna on the dedicated electronic communication device 35 fitted in the wide lower horizontal surface 27 to only react to the blood bag in the compartment 26 concerned without affecting blood bags contained in other compartments 26. The indicator lamps 40, 41, 42 are mounted on the wide horizontal lower surface 27 near the side opening of the compartment 26.

Figures 3A, 3B:
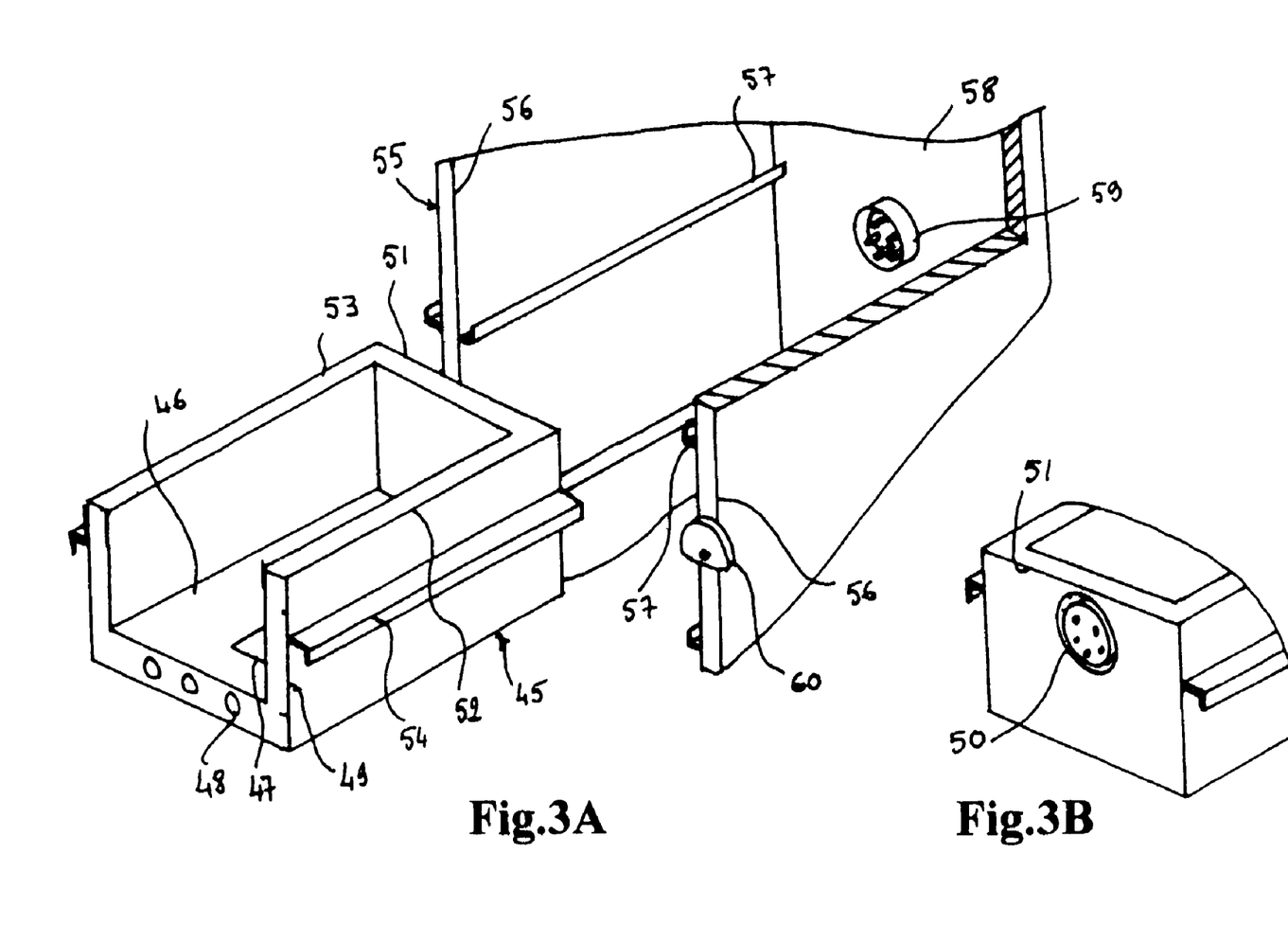
FIGS. 3A and 3B represent another method of making the storage device as per FIG. 2.

In a variant version of the device for implementing the method, the compartments are independent drawers 45 (FIG. 3A) made up of a wide lower surface 46 incorporating a dedicated electronic communications device 47 and the indicator lamps 48 with one side 49 open for inserting the blood bag. The dedicated electronic communication device 47 is connected to a primary connection device 50 (FIG. 3B), incorporated into the small side face that forms the back 51 (FIG. 3A) of the independent drawer 45. The small side faces 52 and 53, which are parallel to each other, possess guide rails 54 on their outside surfaces. A storage unit 55 designed to hold the independent drawers 45 is composed of vertically placed rack arrangements 56 that are parallel to each other at a suitable distance from each other for holding the independent drawers 45 and possessing horizontal slide-ways 57 at regular intervals, on which the guide rails 54 on the independent drawers can run; the bottom of unit 58 of the storage unit 55 contains secondary connecting devices 59 on which fasten the primary connecting devices 50 on the independent drawers 45. The male connectors 59 are connected to the computer. The front side of the rack arrangement 56 may be fitted with a locking device 60 for holding the independent drawers 45 in place.

The invention claimed is:

1. A method of qualifying, re-qualifying and disqualifying a blood bag that includes a silicon chip and an antenna capable of communicating with plural different electronic communication devices, the method comprising:
    providing a plurality of different electronic communication devices;
    arranging one of the plurality of different electronic communication devices on a weighing and stirring device;
    establishing a maximum value of an ageing index to determine when the blood bag is disqualified;
    obtaining a value of the ageing index from the silicon chip at successive moments in time using another of the plurality of different electronic communication devices;
    after the establishing of the maximum value and the obtaining, entering on the silicon chip the value of the ageing index as the ageing index evolves progressively from when blood is collected from a donor towards the maximum value, which, when reached, leads to the blood bag being disqualified;
    calculating, in a health-care institution and at different points in a period of time, the value of the ageing index using a pre-determined ageing model and by taking into account the following:
    bacteriological analyses;
    the value of the ageing index at the beginning of the period;
    a duration of the period; and
    environmental characteristics of the blood bag during the period under consideration;
    re-qualifying the blood bag in the health-care institution when the value of the ageing index of the blood bag is lower than the maximum value and when a new value of the ageing index is recorded on the silicon chip; and
    disqualifying the blood bag when the ageing index reaches the maximum value,
    wherein the re-qualifying occurs when the blood bag enters or leaves a controlled atmosphere chamber and the calculating occurs at successive times between the time the blood is collected and when a patient is transfused with the blood contained in the blood bag,
    wherein the re-qualifying takes place automatically in the controlled atmosphere chamber and occurs when the blood bag returns to the controlled atmosphere chamber,
    wherein, when the blood bag is removed from the controlled atmosphere chamber, the chip contains the value of the last ageing index calculated as well as the date and time that this was done, and
    wherein the pre-determined ageing model takes account of the following conditions under which the blood bag is manipulated:
    blood collection;
    constituent centrifugation and separation; and
    transport under controlled atmosphere between a transfusion center and the health care institution.

2. A method of qualifying, re-qualifying and disqualifying a blood bag that includes a permanently attached a silicon chip fitted with a loop antenna capable of communicating with electronic communication devices, the method comprising:
    providing an electronic communication device;
    arranging the electronic communication device on a weighing and stirring device;
    establishing an ageing index of the blood bag when blood is collected from a donor in a blood transfusion center;
    establishing a maximum value of the ageing index to determine when the blood bag is disqualified;
    after the establishing of the ageing index and the maximum value, entering on the silicon chip, using another electronic communication device, a value of the ageing index as the ageing index evolves progressively towards the maximum value, which, when reached, leads to the blood bag being disqualified;
    calculating the value of the ageing index between two successive moments in time of a period of time by taking into account the following:
    bacteriological analyses;
    the value of the ageing index at the beginning of the period;
    a duration of the period; and
    environmental characteristics of the blood bag during the period under consideration;
    re-qualifying the blood bag when the value of the ageing index of the blood bag is lower than the maximum value and when a new value of the ageing index is recorded on the silicon chip; and disqualifying the blood bag when the ageing index reaches the maximum value, wherein the re-qualifying takes place automatically in a controlled atmosphere chamber and occurs when the blood bag returns to the controlled atmosphere chamber, wherein the ageing index is calculated when the blood bag enters or leaves the controlled atmosphere chamber and when a patient is transfused with the blood contained in the blood bag, wherein a new ageing index value is entered in the silicon chip after each calculation, wherein, when the blood bag is removed from the controlled atmosphere chamber, the chip contains the value of the last ageing index calculated as well as the date and time that this was done, and wherein the calculating utilizes a pre-determined ageing model which takes account of the following conditions under which the blood bag is manipulated:
blood collection;
constituent centrifugation and separation; and
transport under controlled atmosphere between the blood transfusion center and a health care institution.

3. A method of qualifying, re-qualifying and disqualifying a blood bag that includes a silicon chip and a loop antenna capable of communicating with a plurality of electronic communication devices, the method comprising:

providing a plurality of electronic communication devices;

arranging one of the plurality of electronic communication devices on a weighing and stirring device;

establishing a maximum value of the ageing index to determine when the blood bag is disqualified;

obtaining a value of the ageing index from the silicon chip at successive moments in time;

after the establishing of the maximum value and the obtaining, entering on the silicon chip the value of the ageing index as the ageing index evolves progressively from when blood is collected from a donor in a blood transfusion center towards the maximum value, which, when reached, leads to the blood bag being disqualified;

calculating, at different points in a period of time, the value of the ageing index by taking into account the following:
bacteriological analyses;
the value of the ageing index at the beginning of the period;
a duration of the period; and
environmental characteristics of the blood bag during the period under consideration;

re-qualifying the blood bag when the value of the ageing index of the blood bag is lower than the maximum value and when a new value of the ageing index is recorded on the silicon chip; and disqualifying the blood bag when the ageing index reaches the maximum value, wherein the re-qualifying takes place automatically in a controlled atmosphere chamber and occurs when the blood bag returns to the controlled atmosphere chamber, wherein the calculating occurs when the blood bag enters or leaves the controlled atmosphere chamber and when a patient is transfused with the blood contained in the blood bag, wherein, when the blood bag is removed from the controlled atmosphere chamber, the chip contains the value of the last ageing index calculated as well as the date and time that this was done, wherein the ageing index is updated in a health-care institution successively between the time the blood is collected and the time when the blood is transfused, wherein the calculating utilizes a pre-determined ageing model which takes account of the following conditions under which the blood bag is manipulated:
blood collection;
constituent centrifugation and separation; and
transport under controlled atmosphere between the blood transfusion center and the health care institution.

\* \* \* \* \*